(12) United States Patent
Brockmann et al.

(10) Patent No.: US 11,147,615 B2
(45) Date of Patent: Oct. 19, 2021

(54) ELECTRODE UNIT FOR A MEDICAL RESECTOSCOPE

(71) Applicant: OLYMPUS WINTER & IBE GMBH, Hamburg (DE)

(72) Inventors: Christian Brockmann, Hollenstedt (DE); Jun Miki, Tokyo (JP)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 485 days.

(21) Appl. No.: 16/038,355

(22) Filed: Jul. 18, 2018

(65) Prior Publication Data
US 2019/0038341 A1 Feb. 7, 2019

(30) Foreign Application Priority Data
Aug. 4, 2017 (DE) .................. 10 2017 117 749.3

(51) Int. Cl.
*A61B 18/12* (2006.01)
*A61B 18/14* (2006.01)
(Continued)

(52) U.S. Cl.
CPC ........ *A61B 18/149* (2013.01); *A61B 18/1206* (2013.01); *A61B 18/1477* (2013.01);
(Continued)

(58) Field of Classification Search
CPC .............. A61B 18/1477; A61B 18/149; A61B 2018/00083; A61B 2018/00517;
(Continued)

(56) References Cited

U.S. PATENT DOCUMENTS 5,196,011 A * 3/1993 Korth ............... A61B 18/14
606/46
5,658,280 A * 8/1997 Issa ............... A61B 18/1206
606/41
(Continued)

FOREIGN PATENT DOCUMENTS

DE 4032301 A1 4/1992
DE 69836702 T2 10/2007
(Continued)

OTHER PUBLICATIONS

"Your Choice for BPH Resection, Vaporization, Enucleation—Individual PLASMA Treatment". Mar. 1, 2017, URL: https//www.olympus-europa.com/medical/rmt/media/en/Content/Content-MSD/Documents/Brochures/PLASMA_Brochure_EN_16319.pdf, accessed Oct. 8, 2018, pp. 4-19 and Ordering information.
"Surgical Tissue Management System Electrosurgical Generator". Jan. 1, 2014, URL: https://www.olympus-europa.com/medical/rmt/media/en/Content/Content-MSD/Documents/Brochures/ESG-400_Brochure_EN_20140306.pdf, accessed Oct. 8, 2018, pp. 2 and item information.

*Primary Examiner* — Daniel W Fowler
(74) *Attorney, Agent, or Firm* — Oliff PLC

(57) ABSTRACT

An electrode unit for a medical resectoscope for the electrosurgical resection of tissue in a fluid-filled cavity in a patient includes an elongated rod-shaped electrode shaft which on its distal end has an electrode support and a cutting electrode that is fastened to the electrode support and may be acted on by alternating current. A spatula element that is designed for supporting tissue and that extends distally beyond the cutting electrode is situated on the electrode support, the spatula element having two support flanks that extend distally on both sides of the cutting electrode to form outer edges of the spatula element, at least one of the support flanks having an inwardly directed indentation to form a constriction in the area of the cutting electrode.

10 Claims, 3 Drawing Sheets

(51) Int. Cl.
*A61B 1/002* (2006.01)
*A61B 18/00* (2006.01)

(52) U.S. Cl.
CPC ..... *A61B 1/002* (2013.01); *A61B 2018/00083* (2013.01); *A61B 2018/00517* (2013.01); *A61B 2018/00601* (2013.01); *A61B 2018/00982* (2013.01); *A61B 2018/144* (2013.01); *A61B 2018/1407* (2013.01); *A61B 2018/1425* (2013.01); *A61B 2018/1472* (2013.01)

(58) Field of Classification Search
CPC ........... A61B 2018/00601; A61B 2018/00982; A61B 2018/1407; A61B 2018/1425; A61B 2018/144
See application file for complete search history.

(56) References Cited

U.S. PATENT DOCUMENTS 5,749,870 A * 5/1998 Gloth ................... A61B 18/149
606/41
8,771,266 B2 * 7/2014 Shimomura ......... A61B 18/149
606/41

FOREIGN PATENT DOCUMENTS

| EP | 0481310 A1 | 4/1992 |
| EP | 0878167 A2 | 11/1998 |
| EP | 1974683 A1 | 10/2008 |

* cited by examiner

ELECTRODE UNIT FOR A MEDICAL RESECTOSCOPE

CROSS-REFERENCE TO RELATED APPLICATION

This application is based on and claims priority from German Patent Application No. 10 2017 117 749.3, filed on Aug. 4, 2017, which is hereby incorporated by reference in its entirety.

FIELD

The disclosure relates to an electrode unit for a medical resectoscope.

BACKGROUND

Generic electrode units are used in surgery for removal of tissue from the interior of a patient's body. In particular, such electrode units that are equipped with a cutting electrode that may be acted on by high-frequency current are used for urological procedures in which pathological or proliferating tissue is removed from the area of the bladder or the urethra. For such procedures, the electrode unit is connected to a resectoscope whose shaft is advanced through the ureter of the patient until reaching the surgical area. The cutting electrode, which is distally supported on an elongated electrode shaft, may be moved in the distal or proximal direction in the surgical area in a pushing or pulling manner by actuating a handle proximal to the resectoscope. When the cutting electrode is acted on by a high-frequency alternating current, the tissue to be removed, such as a tumor or prostate tissue, may be excised or ablated from the bladder wall or from the urethra by localized generation of heat.

Generic electrode units have a straight, elongated electrode shaft, which on its distal end has an electrode support that is divided, usually in a forked shape, into two support arms, with a cutting electrode, acted on by high-frequency current, situated on the electrode support. The cutting electrode may have different shapes, for example a loop or needle shape, depending on the preference of the surgeon or the intended use of the instrument.

For the transurethral resection of the prostate, the cutting electrode is typically designed as a cutting loop that extends at a right angle to the shaft axis of the electrode shaft, between the two support arms of the electrode support. When the electrode unit is moved back and forth in the outer shaft of the resectoscope, the cutting electrode is distally pushed in front of the opening in the outer tube and pulled tightly against the distal opening in the outer shaft. The prostate tissue is thereby captured by the loop, and by action of a high-frequency current on the loop, is heated so intensely that the electrode cuts through the tissue.

Electrode units of the generic type are also used for removing tumors or other pathological tissue areas from the bladder. Needle-shaped or rod-shaped cutting electrodes are preferably used for this purpose. To prepare for the removal of tissue from the bladder, the bladder wall typically is initially contacted by the cutting electrode, with burning in, around the tissue adhering to the bladder wall in a cyst-like manner, in order to mark the tissue area to be removed. The tissue block to be removed is subsequently cut within the marked area, closely against the bladder wall, and separated from the bladder wall, preferably in a single piece. The cutting electrode is pressed with force beneath the tissue block in order to pretension the cutting area, thus facilitating the separation of the tissue from the bladder wall.

For this en bloc resection using generic electrode units, a surgical technique has become established in which the tissue to be removed with the insulated side edges of the cutting electrode is initially placed under tension with slight lateral tilting of the resectoscope, and is then guided onto the active surface of the cutting electrode by a combination of rotation and axial movement of the electrode unit. Since the cutting electrodes and the connection of the cutting electrodes to the electrode support, in their conventional construction, are not designed for high mechanical loads, forceful pretensioning of the tissue may result in increased wear on the cutting electrode and its fastening structure on the electrode support.

SUMMARY

The object of the present invention, therefore, is to provide an improved electrode unit of the type described at the outset, which allows forceful manipulation of the tissue to be removed without the risk of mechanically overloading the cutting electrode.

This object is achieved by an electrode unit having the features of claim 1. Advantageous embodiments are set forth in the subclaims.

According to the invention, an electrode unit for a medical resectoscope for the electrosurgical resection of tissue in a fluid-filled cavity in a patient, having an elongated rod-shaped electrode shaft which on its distal end has an electrode support and a cutting electrode that is fastened to the electrode support and may be acted on by alternating current, wherein a spatula element that is designed for supporting tissue and that protrudes distally from the cutting electrode is situated on the electrode support, the spatula element having two support flanks that extend distally on both sides of the cutting electrode to form outer edges of the spatula element, at least one of the support flanks having an inwardly directed indentation to form a constriction in the area of the cutting electrode. It is preferably provided that the two support flanks each form an inwardly directed protrusion to allow the advantageous supporting effect on both sides of the cutting electrode, explained in greater detail below.

By use of the spatula element according to the invention, the tissue to be cut may be forcefully pushed to one side, so that the surgical incision made with the cutting electrode may be carried out under pretensioning without mechanically overloading the cutting electrode. Due to the formation of a constriction on the spatula element, the tissue may be held under tension, with the areas of the lateral support flanks situated in front of and behind the constriction and situated at a greater distance from the cutting electrode on the sides, while the tissue area to be cut lies in the constriction, thus reducing the distance from the cutting electrode to the tissue to be cut.

As explained in greater detail below, it is preferably provided that the inwardly directed indentations of the support flanks extend in a plane with the support flanks.

In principle, it is conceivable for the support flanks that form the outer edges of the spatula element to be formed by two wire pieces that are bent inwardly toward the constriction and that extend distally on the sides of the cutting electrode. However, as explained below, the support flanks may also be formed by the edges of a flat spatula body. The particular suitability of the spatula element for mechanically pretensioning the tissue to be removed results from the inwardly directed indentations of the lateral flanks.

When a tumor is removed from the bladder of a patient, the bladder wall is typically initially marked around the tumor with the cutting electrode, acted on by high-frequency current, by flat penetrating contact into the tissue. The spatula element may be used to support the tumor tissue toward the front in order to introduce markings in the bladder wall that lie as closely as possible against the bladder wall. For distally supporting the tissue to be removed, in one embodiment it is provided that the spatula element on its distal end has a straight front flank that extends transversely with respect to the shaft axis. Alternatively, the front flank may be slightly bent, for example with a slight indentation pointing in the proximal direction. The distal front flank may have an outer transverse extension that is wider than the outer transverse distance between the lateral support flanks proximal to their indentations which form the constriction. In particular, the transverse extension of the distal front flank may be wider than the outer transverse distance between the side edges of the electrode support.

The spatula element according to the invention may have a design that is open over the entire surface, for example in the shape of a flat spoon, or that is open between the lateral support flanks. In particular for a full-surface design of the spatula element, it is provided that the spatula element is manufactured as an injection-molded part. In one preferred embodiment, it is provided that the spatula element is formed from a rod that is bent in a looped shape, and whose free ends are fixedly connected to the electrode support. It is provided in particular that the spatula element is made of a wire that is bent in a looped shape. A rod is understood to mean any general form of a longitudinally extended body. A wire is a specialized form of a rod, and is manufactured from a metal that is in particular pliable. A rod is not limited to metal, and may be made of some other material such as a plastic, ceramic, or glass.

The free ends of the bent rod may be joined proximal to the cutting electrode or fastened to the electrode support at a distance from one another. As the result of fastening the spatula element to the electrode support proximal to the cutting electrode, all forces that act on the spatula element during manipulation of the tissue are transmitted to the electrode support. The cutting electrode may thus remain free of load.

In a first variant, it is provided that the electrode support has two support arms on which the cutting electrode is supported, wherein in particular it may be provided that the support arms have a tubular design, and that a wire-shaped body area of the cutting electrode is held in the support arms in an insulated manner in order to increase the mechanical stability of the cutting electrode. In this variant, the free ends of a spatula element that is formed from a bent rod or a bent wire may be fastened in each case to the two support arms of the electrode support. In particular, the free ends may be adhesively bonded or welded to the electrode support.

In tests conducted with different variants of a spatula element, it has been shown that a spatula element that extends straight in a plane in the distal direction is particularly well suited for mechanically supporting the tissue. The straight design of the support flanks ensures that the tissue may lie particularly favorably in the lateral constriction area of the support flanks, so that a preferably large amount of pretensioned tissue can be reached when the electrode unit undergoes slight rotary and pushing movements. In one preferred embodiment, it is therefore provided that the support flanks, including their indentations that form the constriction, extend distally to the cutting electrode in a shared plane.

For a spatula element that is made of a loop-shaped bent wire or a loop-shaped bent rod, according to this embodiment the rod or the wire extends in a shared plane. The inwardly directed indentations of the lateral support flanks also lie in this shared plane. Protrusions or bends of the support flanks transverse to this shared plane are not provided, since with such bulging formations transverse to the plane of the spatula, the tissue captured with the spatula element would be pushed in disadvantageous directions. Above the spatula element, the captured tissue should be able to overlap as freely as possible in order to avoid unnecessary application of force in the pretensioning of the tissue. Below the spatula element, on the side of the cutting electrode, the tissue should extend through the constriction area and as far as possible into the contact zone of the cutting electrode. A downwardly sagging constriction would remove the tissue farther from the root area of the cutting electrode, thus reducing the area of contact of the electrode with the tissue.

In principle, it is conceivable for the spatula element to extend distally to the cutting electrode in a plane that runs parallel to the shaft axis of the electrode shaft. However, tests have shown that a spatula element that is oriented at an angle with respect to the shaft axis of the electrode shaft is particularly well suited for manipulating the tissue to be removed. Therefore, in one preferred embodiment it is provided that the support flanks extend distally to the cutting electrode in a shared plane that runs at an angle to the shaft axis of the electrode shaft, so that the support flanks distal to the cutting electrode extend distally at an angle with respect to the shaft axis of the electrode shaft or at an angle with respect to the direction of extension of the electrode support. It is provided in particular that the support flanks distal to the cutting electrode extend distally at an angle between 0° and 45° with respect to the shaft axis of the electrode shaft or with respect to the direction of extension of the electrode support, in particular tilted in the direction of extension of the cutting electrode. An angle between 0° and 20° is particularly preferred. Very good properties for mechanical support have resulted when the support flanks are inclined in an angular range between 5° and 15°. An inclination angle of 10° is particularly preferred.

In conventional electrode units, the direction of extension of the cutting electrode runs at an angle of 90° with respect to the shaft axis of the electrode shaft or with respect to the direction of extension of the electrode support. In the electrode unit according to the invention, it has been shown that a slight inclination of the cutting electrode in the distal direction in an angular range between 70° and 90°, in particular at an angle of 80°, provides very good cutting results in combination with the spatula element according to the invention. For an inclination angle of less than 90°, the cutting electrode thus extends with a slight distal orientation with respect to the shaft axis of the electrode shaft or with respect to the direction of extension of the electrode support. For a loop electrode, this inclination angle refers to the inclination of the plane in which the cutting loop extends, and for a needle electrode, the inclination angle refers to the inclination angle of the needle axis in which the needle-shaped cutting electrode extends.

The cutting electrode, the same as with conventional electrode units for removal of the prostate, may have a looped design. In particular a semicircular design of the cutting loop is conceivable. In principle, other loop shapes such as an oval, a triangle, or a rectangle are conceivable. When the electrode unit according to the invention is used to remove pathological tissue, such as a tumor from the bladder of the patient, it is preferably provided that the cutting electrode has a needle-shaped design. With a needle-shaped design of the cutting electrode, the body portion of the cutting electrode, which may be brought into cutting contact with the tissue, protrudes from the electrode support in a finger- or pin-like manner. With a needle electrode, it is possible to make precise, grooved incisions through the tissue to be removed, by means of which the tissue is cut up into pieces, whereas with a cutting loop, extensive elongated strips of tissue may be ablated from the contacted surface.

It is preferably provided that the cutting electrode is formed from a wire, in particular a bent wire, whose free ends are fastened to the electrode support. For a needle-shaped design of the cutting electrode, the wire may be bent by 180° at its end that determines the depth of penetration of the electrode into the tissue, and led back with close contact, so that the two legs of the wire that run back and forth form a finger-shaped, in particular a straight needle-shaped, electrode body.

To avoid electrical flashovers between the cutting electrode, which may be acted on by a high-frequency current, and the spatula element, it may be provided that the spatula element is made of an electrically insulating material such as a ceramic or a plastic. It must be ensured that the spatula element withstands the mechanical loads that occur during supporting of the tissue, and that an overload does not result in breakage of the spatula element. Sufficient stability may be provided by an appropriate selection of the material. For a design in which the spatula element has particularly small material thicknesses, a pliable material may also be selected, so that an overload results in elastic deformation, not breakage. At the same time, the spatula element must be robust enough to be able to forcefully support the tissue to be cut. In addition, the spatula element should be easily fastenable to the electrode support. In light of this background, in one preferred embodiment it is therefore provided for the spatula element to be made of a metal, the spatula element being sheathed with an electrically insulating material layer, at least in close proximity to the cutting electrode. Insulation of the spatula element in the area of the cutting electrode is advantageous to prevent direct input of the high-frequency current from the cutting electrode into the spatula element, or a short circuit if the spatula element contacts the cutting electrode. In the design of the spatula element made of a metal wire that borders the cutting electrode at least on the sides, the support flank sections having the inwardly directed protrusions for forming a constriction in the area of the cutting electrode are of particular interest for insulation, since these areas lie particularly close against the cutting electrode.

In principle, insulating only the lateral support flanks in the area of the cutting electrode, and omitting the distal front flank, could be sufficient to avoid undesirable input of the high-frequency current into the spatula element. However, in one embodiment it is conceivable for the spatula element to be sheathed with an electrically insulating material layer in its entire area protruding distally from the cutting electrode, i.e., in particular the lateral support flanks, including the distal front flank.

The metal body of the spatula element may be exposed in an area adjoining the electrode support to allow welding to the electrode support, which likewise is typically made of metal.

According to the invention, also a resectoscope having an electrode unit according to one of claims 1 through 8. Advantages and details of a resectoscope according to the invention also result from the discussions concerning the electrode unit according to the invention.

An electrode unit according to the invention or a resectoscope having an electrode unit according to the invention is used in a method for the electrosurgical resection of tissue in a fluid-filled cavity in a patient, in particular in the bladder of a patient.

In this method, it is provided that the electrode unit is inserted into the cavity, the cutting electrode is acted on by an alternating current, and tissue to be resected or a tissue area in the surroundings of the tissue to be resected is contacted with the cutting electrode that is acted on by the alternating current. When the tissue to be resected is mechanically supported with the aid of the spatula element situated on the electrode unit, a voltage is generated in the tissue which facilitates cutting through the tissue. The cutting area is guided into the constriction of the spatula element and cut into pieces with the cutting electrode.

BRIEF DESCRIPTION OF THE DRAWINGS

Further advantages, features, and particulars of the invention result from the exemplary embodiments described below, with reference to schematic drawings which show the following.

DETAILED DESCRIPTION OF EMBODIMENT(S)

Figure 1:
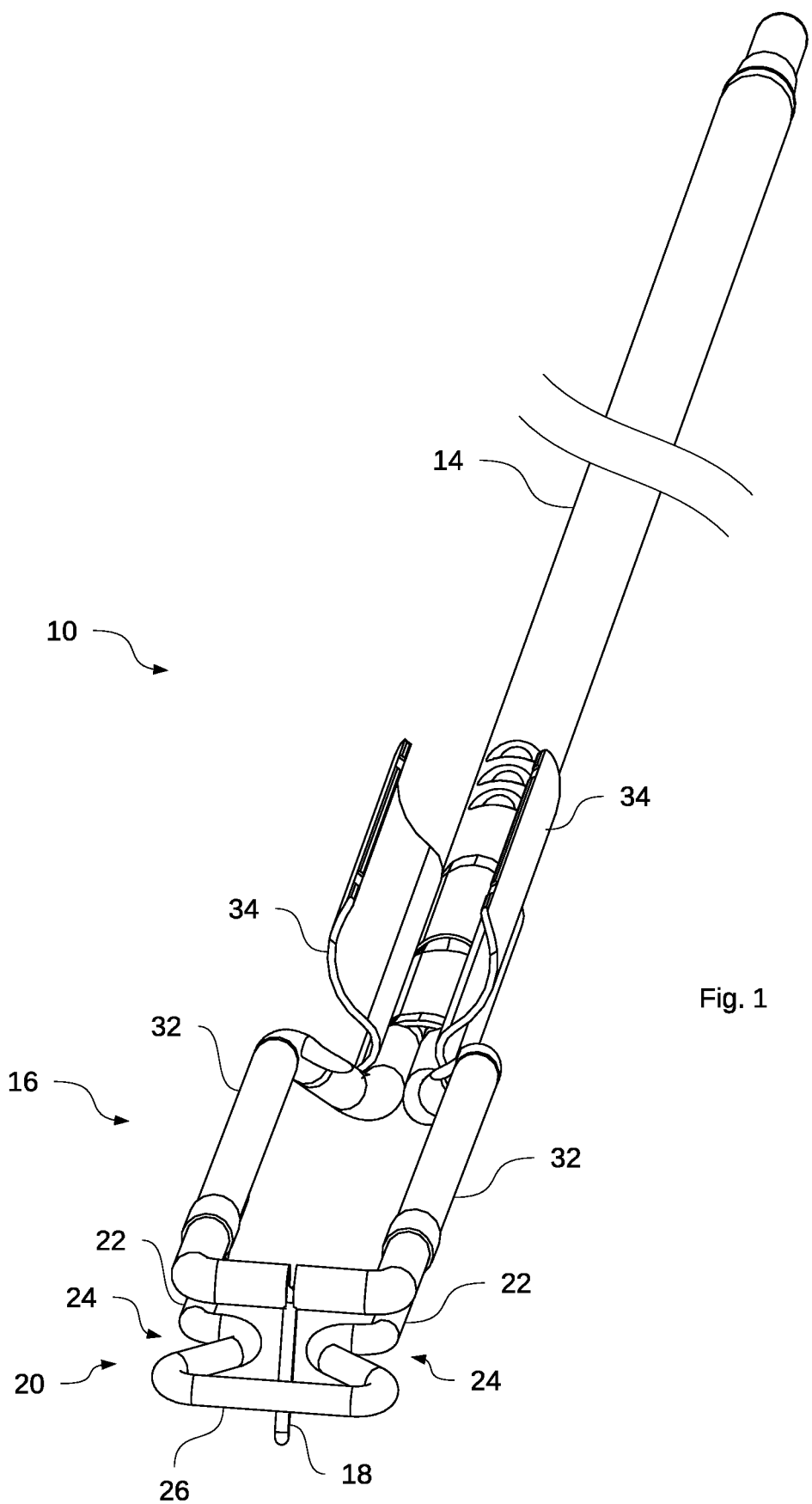
FIG. 1 shows a schematic illustration of an electrode unit according to the invention in a perspective view.

FIG. 1 shows an electrode unit 10 according to the invention for urological resectoscopes, having a straight, elongated rod-shaped electrode shaft 14 which on its distal end has an electrode support 16 with a cutting electrode 18 fastened thereto. In the present example, the electrode support 16 is equipped with two support arms 32, arranged in a fork shape, which at their distal end bear the cutting electrode 18, which in the present case has a needle-shaped design.

An electrical conductor is led from the proximal end of the electrode shaft 14, via the electrode support 16, to the cutting electrode 18 in order for the cutting electrode 18 to be acted on by a high-frequency current. In the proximal end area, the electrode shaft 14 is connectable to a contact point of a resectoscope, by means of which a connection to a high-frequency generator (not illustrated) may be established. As is apparent in particular in combination with FIG. 4, in addition to the cutting electrode 18 the electrode support 16 also bears the spatula element 20 according to the invention, which has two distally extending support flanks 22 that protrude distally from the cutting electrode 18. In the area of the cutting electrode 18, the lateral support flanks 22 have two indentations 24, inwardly directed toward one another, to form a constriction. The spatula element 20 is distally closed off by a front flank 26 that is oriented transversely with respect to the shaft axis of the electrode shaft 14. The front flank 26 may lie in a plane that extends parallel to a support plane A that is spanned by the support arms 32 of the electrode support 16.

Situated proximal to the electrode support 16 on the electrode shaft 14 are two arc-shaped retaining brackets 34 that are provided for displaceably bearing the electron [sic] unit 10 on a shaft or a rod-shaped optics unit (not illustrated) of a resectoscope. The retaining brackets 34 form an approximately forceps-like retaining structure having a free opening in the transverse direction of the electrode shaft 14, so that the retaining elements 34, with elastic expansion, may be clipped to the circumference of a tubular shaft. Alternatively, the retaining structure, which in the present case is formed by the retaining brackets 34, may have a closed tubular shape, so that for a displaceable bearing with a retaining structure designed as a support tube, the electrode unit 10 may be pushed onto a tubular shaft or a rod-shaped optics system of a resectoscope.

Figure 2:
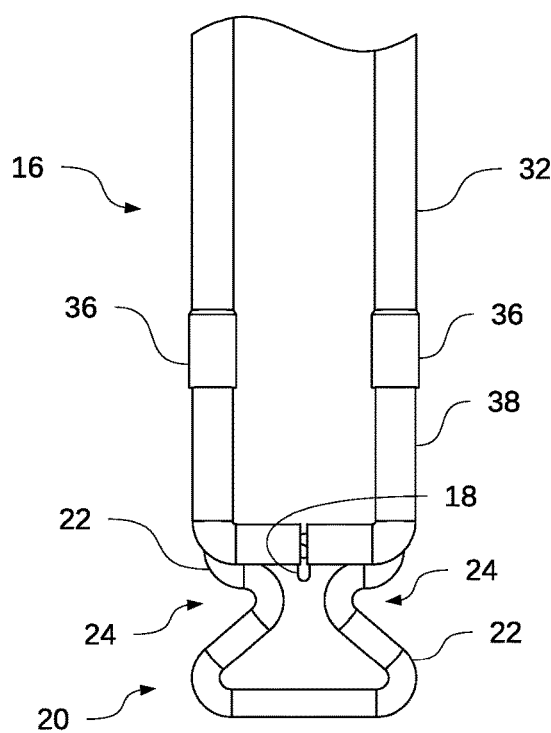
FIG. 2 shows a plan view of the distal area of the electrode unit from FIG. 1, from the top.
Figure 3:
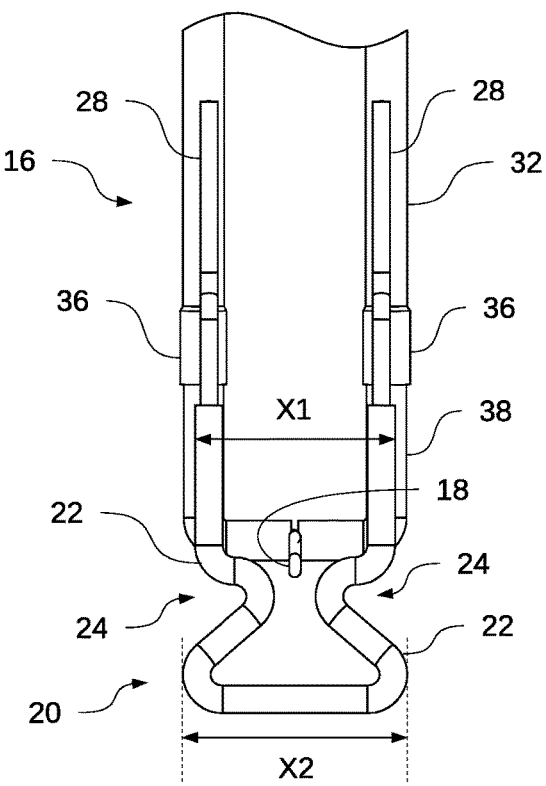
FIG. 3 shows a plan view of the distal area of the electrode unit from FIG. 2, from the bottom.

FIGS. 2 and 3 show a detailed view of the electrode support 16 together with the cutting electrode 18 fastened thereto and the spatula element 20 according to the invention from FIG. 1, in a plan view from above (FIG. 2) and from below (FIG. 3). In the detailed views in FIGS. 2 and 3 it is apparent that the support arms 32 of the electrode support 16, which in the present case extend in parallel to one another, each open into a circumferentially expanded connecting section 36 into which the free ends of the cutting electrode 18, preferably made of a metal wire, are inserted from the distal direction. The metal wire of the cutting electrode 18 which is inserted into the connecting points 36 is encased by an electrically insulating protective sheath 38, except for a contact zone of the cutting electrode 18 which is provided for making an incision in the tissue, in order to prevent undesirable input of high-frequency current into the surrounding tissue in the surgical area, or return conduction of the high-frequency current into the outer wall of the electrode support, which is typically made of metal.

As depicted in FIGS. 2 and 3, the constriction that is formed by the inwardly directed indentations 24 of the lateral support flanks 22 may be arranged in such a way that the narrowest point between the support flanks 22 is positioned distally to the cutting electrode 18. Tissue that is laterally guided into the constriction of the spatula element 20 may thus be easily pretensioned in the distal direction before it is contacted with the cutting electrode 18 by advancement of the electrode unit 10.

As also shown in FIGS. 2 and 3, the free ends 28 of the spatula element 20 which merge into the support flanks 22 in the area of the electrode support initially extend linearly and in parallel in the distal direction before they each begin to bend inwardly, approximately at the level of the cutting electrode 18, in order to subsequently form the indentations 24 for creating the constriction. At a location of the smallest outer transverse distance between the outer edges of the support flanks 22, the support flanks 22 subsequently bend back outwardly in the distal direction and extend distally at an angle until an outer transverse distance X2 between the support flanks 22 is reached that is larger than the greatest transverse distance X1 between the support flanks 22 proximal to the cutting electrode 18.

Figure 4:
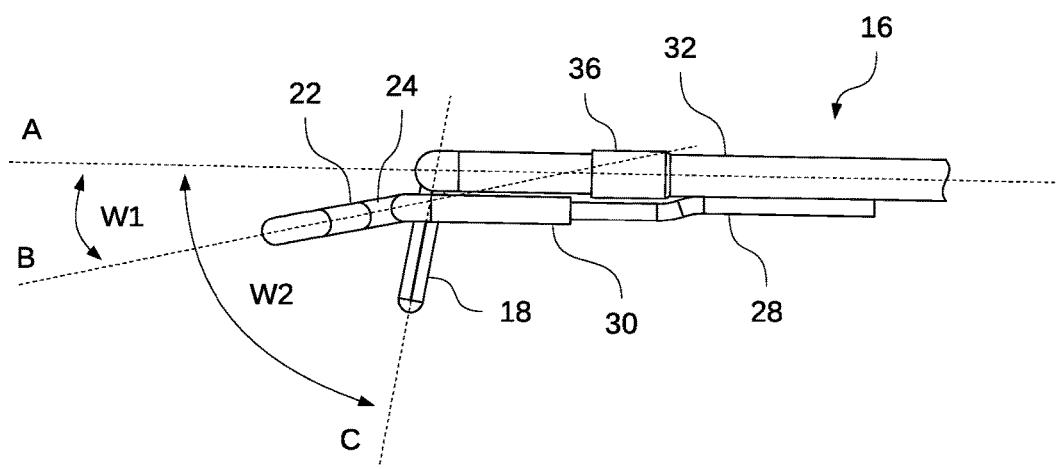
FIG. 4 shows a side view of the electrode support with the spatula element, fastened thereto, from FIGS. 2 and 3.

FIG. 4 shows a side view of the electrode support 16, together with the spatula element 20 from FIGS. 2 and 3 fastened thereto. As shown in FIG. 4, the spatula element 20 extends distally to the cutting electrode 18, preferably in a plane B that is inclined at an angle W1 with respect to a support plane A spanned by the support arms 32 of the electrode support 16, the support plane A preferably being oriented parallel or approximately parallel to the shaft axis of the electrode shaft 14. In the present example, the plane B in which the lateral support flanks 22 of the spatula element 22 extend distally is inclined by approximately 10° with respect to the support plane A, and in particular is tilted in the direction of extension of the cutting electrode 18. To improve the cutting effect during an incision through the tissue with the cutting electrode 18, the support arms 32 and thus the support plane A may have a design that rises slightly upwardly, i.e., opposite the direction of extension of the cutting electrode 18, with respect to the shaft axis of the electrode shaft 14, for example in a range between 0° to 3°, preferably in a range between 0.5° and 2.5°.

The cutting electrode 18 in the present case has a needle-shaped design. The cutting electrode 18 thus protrudes from the electrode support 16 approximately in the manner of a finger. In the present example, the cutting electrode 18 is not oriented at right angles to the support plane A, but, rather, extends at an angle W2 thereto which is less than 90°. As indicated in the present case, the angle W2 between the support plane A and the line of extension C of the cutting electrode 18 may preferably be 80°.

As is also apparent from FIG. 4, the free ends 28 of the spatula element 22 proximal to the connecting points 36 are fastened to the electrode support 16, wherein the free ends 28 proximal to the connecting points 36 are initially guided closely against the support arms 32, and in their distal extension form a step before reaching the circumferentially expanded connecting points 36 of the electrode support 16, in order to provide a distance from the connecting points 36 and the distally adjoining electrode area. This relieves mechanical load on the connecting points 36 and the wire ends of the cutting electrode 18 that are inserted into the connecting points 36. The mechanical forces that act on the spatula element 20 during manipulation of tissue are thus transmitted to the electrode support 16.

In the area of the cutting electrode 18, the spatula element 20 which is preferably made from a bent wire is sheathed with an electrically insulating material layer 30 to prevent direct or indirect input of a high-frequency electrical current of the cutting electrode 18 into the metal body of the spatula element 20, and thus into surrounding tissue or into the outer wall of the electrode support 16. The metallic outer wall of the support arms 32 and optionally also the free ends 28 of the spatula element 16 that are conductively connected to the support arms 32 are preferably used as a return conductor for the high-frequency current that is input during the electrosurgical incision into the tissue. Without insulation of the spatula element 16 in the area of the cutting electrode 18, the high-frequency current would flow directly from the upper end of the cutting electrode 18 into the spatula element 16 surrounding the cutting electrode 18. In addition, for a spatula element 16 made of metal, without suitable insulation there is the risk of a short circuit between the return conductor and the cutting electrode 18 when the cutting electrode 18 and the spatula element 16 make conductive contact (for example, due to bending of the spatula element 16 during forceful manipulation of tissue).

Figure 5:
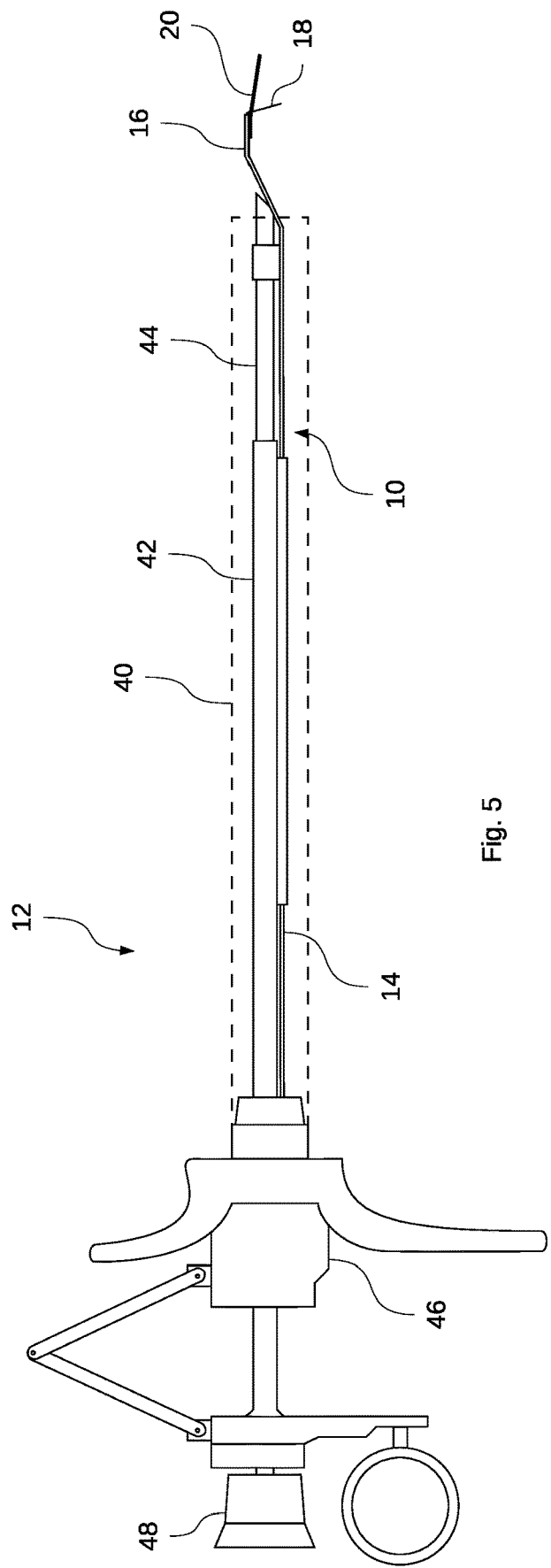
FIG. 5 shows a resectoscope having an electrode unit according to the invention.

FIG. 5 shows a resectoscope 12 with an electrode unit 10 according to the invention that is guided in a cladding tube 40. Within the cladding tube 40, the electrode shaft 14 of the electrode unit 10 is longitudinally displaceably guided on an inner shaft 42 that is used as an optics guide tube. A rod-shaped optics unit 44, inserted into the inner shaft 42, which conducts an image from the distal end area of the inner shaft to a proximal observation point 48, in the present case designed as an eyepiece, is used for observation of the surgical area.

In order to provide further channels for conducting fluid or for guiding work instruments, one or more additional shafts (not illustrated) may be provided outside the cladding tube 40 and/or between the cladding tube 40 and the inner shaft 42 which is used as an optics guide tube. In particular for a continuous flow resectoscope, an additional outer shaft which accommodates the inner shaft 42, the cladding tube 40, and the electrode unit 10 supported in between is generally mounted on the cladding tube 40. The space between the cladding tube 40 and an additional outer shaft is utilized as a further channel for conducting fluid.

In its proximal end area, the electrode shaft 14 is coupled to a carriage 46 that is supported so that it may slide on the inner shaft 42 in a longitudinally displaceable manner. When a handle unit that is coupled to the carriage 46 on the one hand and to the optics guide tube 42 on the other hand is actuated, the electrode support 16 together with the cutting electrode 18 and the spatula element 20 may be axially advanced or retracted.

| List of reference numerals | |
|---|---|
| 10 | electrode unit |
| 12 | resectoscope |
| 14 | electrode shaft |
| 16 | electrode support |
| 18 | cutting electrode |
| 20 | spatula element |
| 22 | support flank |
| 24 | indentation |
| 26 | front flank |
| 28 | free ends of the spatula element |
| 30 | insulating material layer of the spatula element |
| 32 | support arms of the electrode support |
| 34 | retaining brackets |
| 36 | connecting points |
| 38 | protective sheath of the electrode |
| 40 | cladding tube |
| 42 | optics guide tube |
| 44 | optics unit |
| 46 | carriage |
| 48 | eyepiece |
| A | support plane |
| B | plane of extension of the spatula element |
| C | plane or line of extension of the cutting electrode |
| W1 | angle between the support plane and the plane of extension of the spatula element |
| W2 | angle between the support plane and the direction of extension of the cutting electrode |

The invention claimed is:

1. An electrode unit for a medical resectoscope for electrosurgical resection of tissue in a fluid-filled cavity in a patient, the electrode unit comprising:
    an elongated rod-shaped electrode shaft which on its distal end has an electrode support and a cutting electrode that is fastened to the electrode support and to which an alternating current can be applied, wherein:
    a spatula element that is designed for supporting tissue and that extends distally beyond the cutting electrode is situated on the electrode support,
    the spatula element has two support flanks that extend distally on both sides of the cutting electrode to form outer edges of the spatula element,
    at least one of the support flanks has an inwardly directed indentation that is inwardly directed toward the other of the support flanks, to form a constriction in an area of the cutting electrode.
2. The electrode unit according to claim 1, wherein
    the spatula element on its distal end has a straight front flank that extends transversely with respect to a shaft axis of the elongated rod-shaped electrode shaft.
3. The electrode unit according to claim 1, wherein
    the spatula element is formed from a rod that is bent in a looped shape, and whose free ends are fixedly connected to the electrode support.
4. The electrode unit according to claim 1, wherein
    the support flanks extend distally to the cutting electrode in a shared plane.
5. The electrode unit according to claim 4, wherein
    the shared plane extends at an angle with respect to a shaft axis of the elongated rod-shaped electrode shaft, so that the support flanks extend distally to the cutting electrode at an angle with respect to the shaft axis in a distal direction.
6. The electrode unit according to claim 1, wherein
    the cutting electrode has a needle-shaped design.
7. The electrode unit according to claim 1, wherein
    the cutting electrode is formed from a wire, whose free ends are fastened to the electrode support.
8. The electrode unit according to claim 1, wherein
    the spatula element is made of a metal, and
    the spatula element is sheathed with an electrically insulating material layer, at least in close proximity to the cutting electrode.
9. The electrode unit according to claim 1, wherein
    the spatula element is configured such that tissue is guided into the constriction formed by the indentation of the at least one support flank, before being contacted and cut out by the cutting electrode.
10. A resectoscope which includes the electrode unit according to claim 1.

* * * * *